United States Patent
Adair et al.

(10) Patent No.: US 8,500,716 B2
(45) Date of Patent: Aug. 6, 2013

(54) MEDICATION RESERVOIR

(71) Applicants: Randy W. Adair, Valencia, CA (US); Sheldon B. Moberg, Thousand Oaks, CA (US); Chalirmkiert Srisathapat, Sun Valley, CA (US)

(72) Inventors: Randy W. Adair, Valencia, CA (US); Sheldon B. Moberg, Thousand Oaks, CA (US); Chalirmkiert Srisathapat, Sun Valley, CA (US)

(73) Assignee: Medtronic MiniMed, Inc., Northridge, CA (US)

(*) Notice: Subject to any disclaimer, the term of this patent is extended or adjusted under 35 U.S.C. 154(b) by 0 days.

(21) Appl. No.: 13/622,183

(22) Filed: Sep. 18, 2012

(65) Prior Publication Data

US 2013/0018357 A1    Jan. 17, 2013

Related U.S. Application Data

(63) Continuation of application No. 13/155,641, filed on Jun. 8, 2011, now Pat. No. 8,303,572, which is a continuation of application No. 12/361,203, filed on Jan. 28, 2009, now Pat. No. 7,981,105, which is a continuation of application No. 10/923,133, filed on Aug. 20, 2004, now Pat. No. 7,628,782, which is a continuation of application No. 10/328,393, filed on Dec. 23, 2002, now Pat. No. 7,658,734, which is a continuation of application No. 09/428,818, filed on Oct. 28, 1999, now Pat. No. 6,585,695.

(60) Provisional application No. 60/106,237, filed on Oct. 29, 1998.

(51) Int. Cl.
*A61M 25/16* (2006.01)

(52) U.S. Cl.
USPC .......................................................... 604/533

(58) Field of Classification Search
USPC ................. 604/181, 183, 523, 533, 535, 240, 604/241
See application file for complete search history.

(56) References Cited

U.S. PATENT DOCUMENTS

| | | |
|---|---|---|
| 3,623,474 A | 11/1971 | Heilman et al. |
| 3,701,345 A | 10/1972 | Heilman et al. |

(Continued)

FOREIGN PATENT DOCUMENTS

| | | |
|---|---|---|
| DE | 2240694 | 8/1972 |
| DE | 9013145 | 11/1990 |

(Continued)

OTHER PUBLICATIONS

Roche Diagnostics GmbH, Opposition against European patent EP 1 642 615 B1 (Appl. No. 05026578.4), Nov. 9, 2011, Munich, Germany.

(Continued)

*Primary Examiner* — Quynh-Nhu H Vu
(74) *Attorney, Agent, or Firm* — Gates & Cooper LLP

(57) ABSTRACT

A method and apparatus for a connection interface between a reservoir or syringe, infusion set tubing, and an infusion pump is provided. A base is provided which is adapted to receive a reservoir. The base has a base engagement member, such as a detent, projecting therefrom. A cap is provided which is adapted to receive the base. The cap includes a first cap engagement member, such as a detent opening, which is adapted to removably engage the base detent. The cap further includes a second cap detent opening which is adapted to removably engage the base detent. A piercing member, such as a needle, is disposed in the interior of the cap in such a manner that the needle is separated from the reservoir septum when the base detent is in the first cap detent opening, and the needle pierces the reservoir septum when the base detent is in the second cap detent opening. When the reservoir, the base and the cap are connected to form an integrated unit, this unit is then capable of being inserted and secured in the infusion pump housing.

20 Claims, 14 Drawing Sheets

U.S. PATENT DOCUMENTS

| | | | |
|---|---|---|---|
| 4,076,285 A | 2/1978 | Martinez | |
| 4,084,588 A | 4/1978 | Koenig | |
| 4,267,836 A | 5/1981 | Whitney et al. | |
| 4,274,407 A | 6/1981 | Scarlett | |
| 4,278,188 A | 7/1981 | Stephenson et al. | |
| 4,444,546 A | 4/1984 | Pazemenas | |
| 4,468,221 A | 8/1984 | Mayfield | |
| 4,562,751 A | 1/1986 | Nason et al. | |
| 4,564,054 A | 1/1986 | Gustavsson | |
| 4,576,211 A | 3/1986 | Valentini et al. | |
| 4,585,439 A | 4/1986 | Michel | |
| 4,588,403 A | 5/1986 | Weiss et al. | |
| 4,601,491 A | 7/1986 | Bell, Jr. et al. | |
| 4,610,469 A | 9/1986 | Wolff-Mooij | |
| 4,619,646 A | 10/1986 | Hernandez et al. | |
| 4,678,408 A | 7/1987 | Nason et al. | |
| 4,685,903 A | 8/1987 | Cable et al. | |
| 4,744,790 A | 5/1988 | Jankowski et al. | |
| 4,747,824 A | 5/1988 | Spinello | |
| 4,749,109 A | 6/1988 | Kamen | |
| 4,752,292 A | 6/1988 | Lopez et al. | |
| 4,834,744 A | 5/1989 | Ritson | |
| 4,931,816 A | 6/1990 | Kamo et al. | |
| 4,936,833 A | 6/1990 | Sams | |
| 4,952,205 A | 8/1990 | Mauerer et al. | |
| 5,062,832 A | 11/1991 | Seghi et al. | |
| 5,080,653 A | 1/1992 | Voss et al. | |
| 5,087,250 A | 2/1992 | Lichte et al. | |
| 5,097,122 A | 3/1992 | Colman et al. | |
| 5,100,394 A * | 3/1992 | Dudar et al. | 604/537 |
| 5,121,019 A | 6/1992 | Pradler | |
| 5,137,524 A | 8/1992 | Lynn et al. | |
| 5,188,610 A | 2/1993 | Rains | |
| 5,201,717 A | 4/1993 | Wyatt et al. | |
| 5,219,099 A | 6/1993 | Spence et al. | |
| 5,242,411 A | 9/1993 | Yamamoto et al. | |
| 5,254,096 A | 10/1993 | Rondelet et al. | |
| 5,261,572 A * | 11/1993 | Strater | 222/215 |
| 5,279,569 A | 1/1994 | Neer et al. | |
| 5,292,306 A | 3/1994 | Wynkoop et al. | |
| 5,295,657 A | 3/1994 | Atkinson | |
| D347,894 S | 6/1994 | Hansen et al. | |
| 5,330,450 A | 7/1994 | Lopez | |
| 5,334,179 A | 8/1994 | Poli et al. | |
| 5,374,256 A | 12/1994 | Kriesel | |
| 5,389,078 A | 2/1995 | Zalesky et al. | |
| 5,423,753 A | 6/1995 | Fowles et al. | |
| 5,466,218 A | 11/1995 | Srisathapat et al. | |
| 5,505,709 A | 4/1996 | Funderburk et al. | |
| 5,514,090 A | 5/1996 | Kriesel et al. | |
| 5,545,152 A | 8/1996 | Funderburk et al. | |
| 5,549,574 A | 8/1996 | Townsend | |
| 5,554,134 A | 9/1996 | Bonnichsen | |
| 5,599,323 A | 2/1997 | Bonnichsen et al. | |
| 5,611,785 A | 3/1997 | Mito et al. | |
| D380,262 S | 6/1997 | Van Funderburk et al. | |
| 5,637,095 A | 6/1997 | Nason et al. | |
| 5,647,845 A * | 7/1997 | Haber et al. | 604/32 |
| 5,647,853 A | 7/1997 | Feldmann et al. | |
| 5,722,545 A | 3/1998 | Rinne | |
| 5,779,675 A | 7/1998 | Reilly et al. | |
| 5,810,792 A | 9/1998 | Fangrow et al. | |
| 5,817,082 A | 10/1998 | Niedospial, Jr. et al. | |
| 5,871,500 A | 2/1999 | Jepson et al. | |
| 5,895,383 A | 4/1999 | Niedospial, Jr. | |
| 5,897,526 A | 4/1999 | Vaillancourt | |
| 5,947,935 A | 9/1999 | Rhinehart et al. | |
| 5,989,215 A | 11/1999 | Delmotte et al. | |
| 5,993,423 A * | 11/1999 | Choi | 604/155 |
| 5,993,425 A | 11/1999 | Kriesel | |
| 6,090,082 A | 7/2000 | King et al. | |
| 6,488,650 B1 | 12/2002 | Epstein et al. | |
| 6,585,695 B1 | 7/2003 | Adair et al. | |
| 7,628,772 B2 | 12/2009 | McConnell et al. | |
| 7,628,782 B2 | 12/2009 | Adair et al. | |
| 7,658,734 B2 | 2/2010 | Adair et al. | |

FOREIGN PATENT DOCUMENTS

| | | |
|---|---|---|
| DE | 19717107 | 11/1998 |
| EP | 0544653 | 1/1989 |
| EP | 0453212 | 10/1991 |
| EP | 0980687 | 2/2000 |
| EP | 1642615 | 4/2006 |
| FR | 2628639 | 9/1989 |
| JP | 5-74545 | 10/1993 |
| WO | 91/16938 | 11/1991 |
| WO | 9800157 | 10/1998 |
| WO | 99/10032 | 3/1999 |
| WO | 02/076527 | 10/2002 |

OTHER PUBLICATIONS

Ulrike Thurm, Insulinpumpenfibel oder . . . bei Dir piept's ja, 1996, 2. Aufl., Germany. (Primer on insulin pumps).

Disetronic, Adapter Komplett NLL, Jun. 9, 1994, Zeichnungsnummer 1238V003.01, Germany. (Schematic diagram of an insulin pump adapter).

Disetronic, Adapter NLL2, Jun. 9, 1994, Zeichnungsnummer 300.0184.04, Germany. (Schematic diagram of an insulin pump adapter with a closure element).

Disetronic, Die H-iron plus Gebrauchsanleitung, Feb. 1998, Germany. (Instruction manual for an insulin pump).

Erklärung von Herrn Reto Aeschlimann, Oct. 26, 2011, Germany and/or Switzerland. (Statement by Reto Aeschlimann regarding a primer on insulin pumps and specific insulin pumps).

Erklärung von Frau Ulrike Thurm, Nov. 2, 2011, Germany and/or Switzerland. (Statement by Ulrike Thurm regarding a primer on insulin pumps and specific insulin pumps).

Disetronic, Die H-Tron plus Reiseanleitung Kurzfassung, Sep. 1997, Germany. (Instruction manual for an insulin pump).

Elke Austenat and Tilman Stahl, Insulinpumpentherapie, 1989, pp. 16-42, Walter de Gruyter & Co., Berlin, Germany. (Primer on insulin pump therapy).

Disetronic, Disetronic Pumpen-Forum, Jun. 1996, Germany. (Insulin pump forum newsletter).

Elke Austenat, Das Insulinpumpen-Buch, 1998, pp. 68-79, Blackwell Wissenschafts-Verlag, Berlin, Germany. (Book on insulin pumps and physiologic insulin supplies).

Non-Final Office Action dated Oct. 27, 2009 issued in U.S. Appl. No. 10/607,340, filed Jun. 26, 2003.

Final Office Action dated Jul. 17, 2009 issued in U.S. Appl. No. 10/607,340, filed Jun. 26, 2003.

Non-Final Office Action dated Dec. 23, 2008 issued in U.S. Appl. No. 10/607,340, filed Jun. 26, 2003.

Final Office Action dated May 30, 2008 issued in U.S. Appl. No. 10/607,340, filed Jun. 26, 2003.

Non-Final Office Action dated Nov. 28, 2007 issued in U.S. Appl. No. 10/607,340, filed Jun. 26, 2003.

Non-Final Office Action dated May 4, 2007 issued in U.S. Appl. No. 10/607,340, filed Jun. 26, 2003.

Non-Final Office Action dated Oct. 11, 2006 issued in U.S. Appl. No. 10/607,340, filed Jun. 26, 2003.

Non-Final Office Action dated Apr. 21, 2006 issued in U.S. Appl. No. 10/607,340, filed Jun. 26, 2003.

Non-Final Office Action dated Jul. 12, 2010 issued in U.S. Appl. No. 12/631,377, filed Dec. 4, 2009.

Non-Final Office Action dated Dec. 15, 2010 issued in U.S. Appl. No. 12/631,377, filed Dec. 4, 2009.

Final Office Action dated Jun. 9, 2011 issued in U.S. Appl. No. 12/631,377, filed Dec. 4, 2009.

Non-Final Office Action dated Jan. 26, 2012 issued in U.S. Appl. No. 12/631,377, filed Dec. 4, 2009.

Disetronic, Die H-Tron plus Gebrauchsanleitung, Feb. 1998, Germany. (Instruction manual for an insulin pump).

PCT Application PCT/US99/25414, Search Report mailed Feb. 2, 2000.

PCT Application PCT/US99/25413, Search Report mailed Mar. 7, 2000.

\* cited by examiner

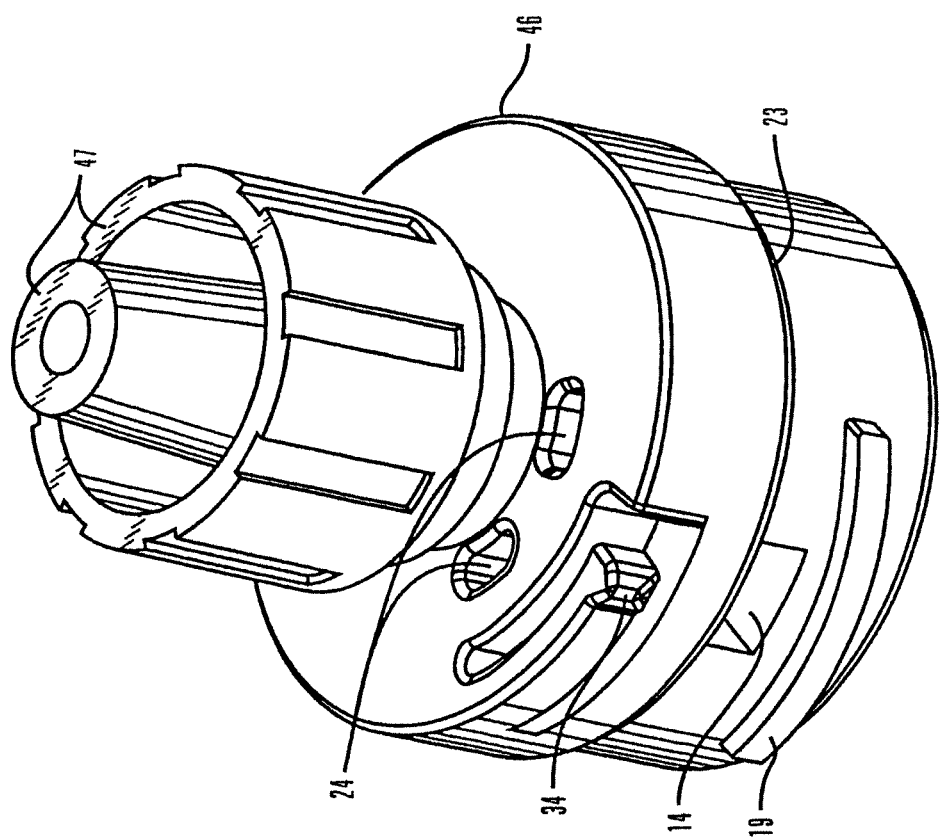

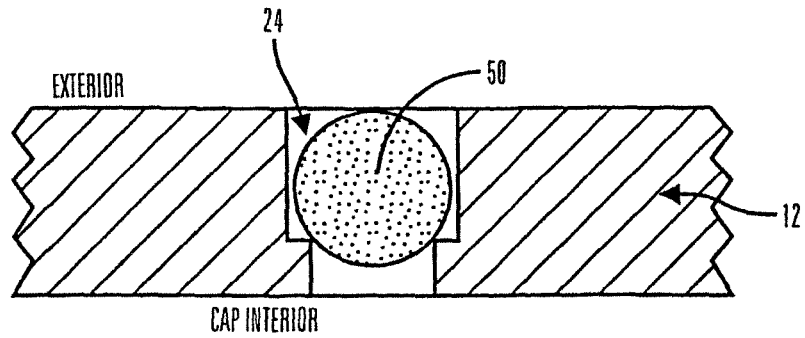
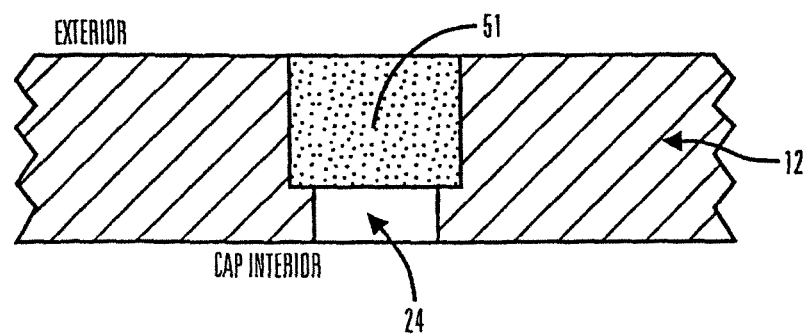
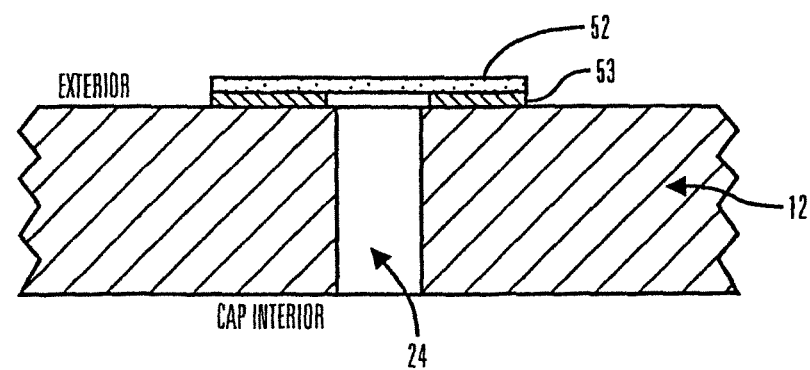

MEDICATION RESERVOIR

CROSS-REFERENCE TO RELATED APPLICATIONS

This application claims priority from U.S. patent application Ser. No. 13/155,641, filed Jun. 8, 2011, which claims priority from U.S. patent application Ser. No. 12/361,203, filed Jan. 28, 2009, which claims priority from U.S. patent application Ser. No. 10/923,133, filed Aug. 20, 2004, now U.S. Pat. No. 7,628,782, which claims priority from U.S. patent application Ser. No. 10/328,393, filed Dec. 23, 2002, now U.S. Pat. No. 7,658,734, which claims priority from U.S. patent application Ser. No. 09/428,818, filed Oct. 28, 1999, now U.S. Pat. No. 6,585,695, which claims priority from provisional patent application No. 60/106,237 which was filed on Oct. 29, 1998 and which is incorporated herein by reference.

BACKGROUND OF THE INVENTION

1. Field of the Invention

This invention relates generally to improvements in syringe and reservoir interfaces for use in infusion pumps such as those used for controlled delivery of medication to a patient. More specifically, this invention relates to an improved connection interface between a reservoir or syringe, infusion set tubing, and an infusion pump.

2. Description of the Related Art

Infusion pump devices and systems are relatively well-known in the medical arts, for use in delivering or dispensing a prescribed medication such as insulin to a patient. In one form, such devices comprise a relatively compact pump housing adapted to receive a syringe or reservoir carrying a prescribed medication for administration to the patient through infusion tubing and an associated catheter.

The infusion pump includes a small drive motor connected via a lead screw assembly for motor-driven advancement of a reservoir piston to administer the medication to the user. Programmable controls are normally provided for operating the drive motor continuously or at periodic intervals to obtain a closely controlled and accurate delivery of the medication over an extended period of time. Such infusion pumps are utilized to administer insulin and other medications, with exemplary pump constructions being shown and described in U.S. Pat. Nos. 4,562,751; 4,678,408; 4,685,903; 5,080,653 and 5,097,122, which are incorporated by reference herein.

Infusion pumps of the general type described above have provided significant advantages and benefits with respect to accurate delivery of medication or other fluids over an extended period of time. The infusion pump can be designed to be relatively compact as well as water resistant, and may thus be adapted to be carried by the user, for example, by means of a belt clip. As a result, important medication can be delivered to the user with precision and in an automated manner, without significant restriction on the user's mobility or life-style, including the ability to participate in water sports.

Infusion sets refer to the tubing and connection apparatus which provide a path for the medication to flow from the reservoir or syringe located in the pump to the user. The connectors for attaching the infusion set tubing to the reservoirs can take various forms. A luer connection is a commonly used connection method. Nevertheless, it remains desirable to develop improved designs of connection methods to facilitate infusion procedures and to provide suitable interface connections which are water resistant so as to permit a user to participate in water sports.

SUMMARY OF THE PREFERRED EMBODIMENTS

An apparatus for connecting a reservoir having a septum and a base to a conduit, such as infusion set tubing, is provided. In certain aspects of the present invention, the apparatus comprises a cap and a releasable coupler which is adapted to releasably couple the base to the cap in one of two positions. A piercing member, such as a needle, is coupled to the conduit. The needle is disposed in the cap in a position other than the interior of the reservoir when the base is in the first position. The needle is further disposed to pierce the reservoir septum when the base is in the second position.

In another embodiment, the apparatus is used for connecting a reservoir having a septum and a base to a housing as well as to a conduit. The housing has a housing engagement member, such as a thread. The apparatus comprises a cap and a releasable coupler which is adapted to releasably couple the base to the cap in one of two positions. A piercing member, such as a needle, is releasably coupled to the conduit. The needle is disposed in the cap in a position other than the interior of the reservoir when the base is in the first position. The needle is further disposed to pierce the reservoir septum when the base is in the second position. The cap further includes an engagement member, such as a thread, which is adapted to engage with the housing engagement member.

In another embodiment, the cap further includes a vent port which is covered with hydrophobic material. This permits air to pass through the cap while preventing water from doing so.

BRIEF DESCRIPTION OF THE DRAWINGS

FIG. 13 is a perspective view of an alternative embodiment of a cap used as a medication reservoir connection interface apparatus.

FIGS. 14a-14c are cross-sectional views of various embodiments of venting ports for use with a reservoir connection interface apparatus or adapter.

DETAILED DESCRIPTION OF THE PREFERRED EMBODIMENTS

Figure 1:
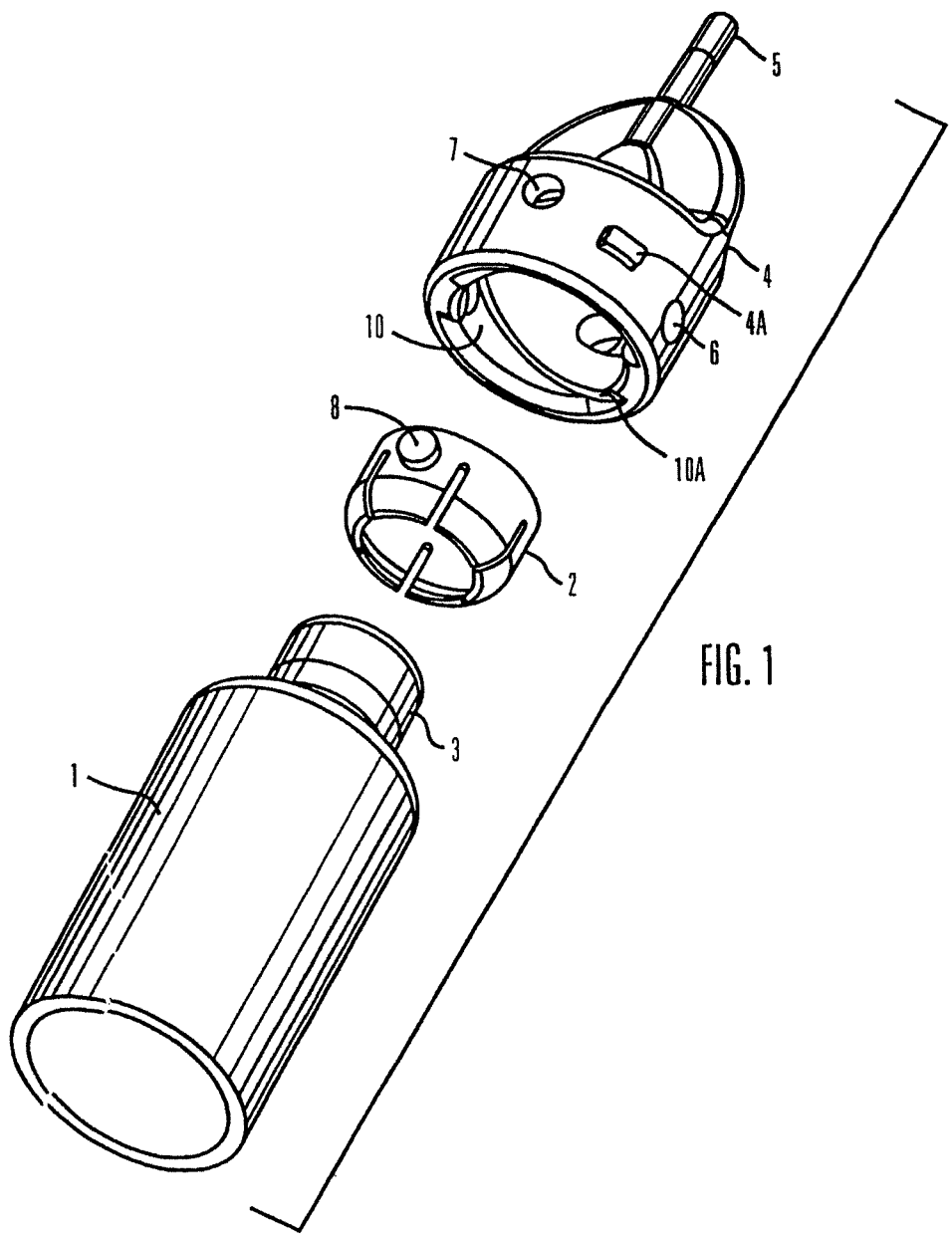
FIG. 1 is an exploded, perspective view of a medication reservoir connection interface apparatus.

In the following description, reference is made to the accompanying drawings which form a part hereof and which illustrate several embodiments of the present invention. It is understood that other embodiments may be utilized and structural and operational changes may be made without departing from the scope of the present invention.

As shown in the drawings for purposes of illustration, the invention is embodied in an interface for connecting a syringe or a medication reservoir to a conduit, such as infusion set tubing or an external needle, as well as to an infusion pump. In a one embodiment, a base is provided which is adapted to receive a reservoir. A cap is provided which is adapted to be releasably coupled to the base in one of two positions. The releasable coupler comprises a pair of detents projecting from the base and two pairs of detent openings in the cap which are adapted to removably engage the base detents.

A piercing member, such as a needle, is disposed in the interior of the cap in such a manner that the needle is separated from the reservoir septum when the base detents are in the first pair of cap detent openings, and the needle pierces the reservoir septum when the base detents are in the second pair of cap detent openings. When the reservoir, the base and the cap are connected, an integrated unit is formed which is then capable of being inserted in the infusion pump housing. Engagement members, such as threads, for the cap and the pump housing are used to secure the integrated unit in the housing.

Figure 2:
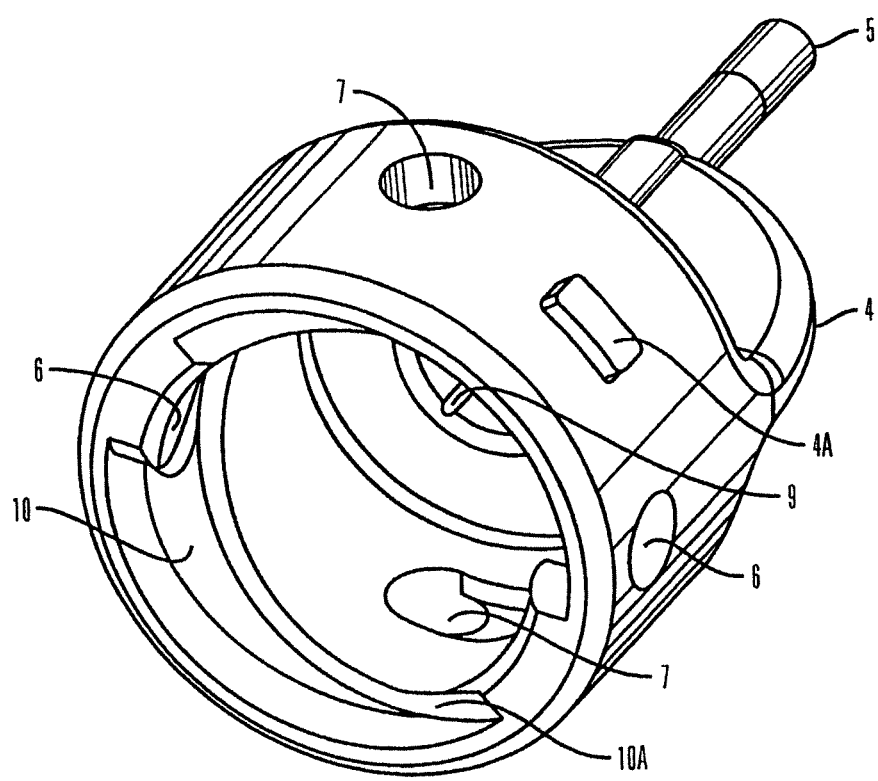
FIG. 2 is a perspective view of a cap used as a medication reservoir connection interface apparatus.

FIGS. 1 and 2 show an infusion set connector interface for attachment to a medication reservoir. The connector interface is comprised of a base 2 and a cap 4. The cap 4 includes a needle 9 located internal to the cap housing. FIG. 1 is an exploded view, and therefore, the base 2 would normally be fixedly attached to a reservoir 1 by securing it around the swage 3. However, alternative embodiments of the present invention include a removable base so that the connector interface could be used with standard reservoirs, cartridges or syringes which were not initially manufactured with the base attached.

The cap 4 portion of the connector interface is removably attached to the base 2 with a releasable coupler. In one embodiment, the releasable coupler is comprised of detents formed on the base 2 and detent openings disposed in the cap 4. Two detents 8 are disposed on the sides of the base 2 and are spaced 180° radially apart. Only one detent 8 is shown in FIG. 1. The detents 8 are sized to fit in the two lower detent openings 6, or alternatively, in the two upper detent openings 7 which are formed in the cap 4. As with the pair of detents 8, each of the lower detent openings 6 and each of the upper detent openings 7, respectively, are radially spaced apart by 180°.

In operation, the base 2 and the reservoir 1 form an integrated unit which in turn is to be connected to the cap 4. In connecting this integrated base/reservoir unit to the cap 4, the base 2 is inserted into the lower end of the cap 4 until the detents 8 snap into the lower detent openings 6. This is accomplished by moving the detents 8 over internal cam surfaces 10 toward the lower detent openings 6. The cam surfaces act as ramps which compress the detents 8 sufficiently to permit them to snap into the lower detent openings 6. Internal threads 10a guide the detents 8 into position.

When the base/reservoir unit is in this first, lower position, the needle 9 is positioned apart from the septum (not shown) of the reservoir 1. Thus the needle does not pierce the septum while the base/reservoir unit is in this first position. When the base/reservoir unit is connected to the cap in this fashion, an integrated cap/base/reservoir unit is thereby formed. Such an integrated cap/base/reservoir unit can be sold or stored for long periods of time in this fashion. Alternatively the end user could assemble this unit shortly prior to placing it in the pump for use.

When the user desires to insert the cap/base/reservoir unit in the pump housing and commence dispensing the medication through a conduit, such as insertion set tubing 5, the base 2 is moved to the second position within the cap 4. This is accomplished by twisting the base/reservoir unit while pushing it further into the cap 4. The detents 8 disengage from the lower detent openings 6 and engage into the upper detent openings 7. Additional internal threads 10a of the cap 4 serve to guide the detents 8 over additional cam surfaces 10 from their first position in the lower detent openings 6 to the second position in the upper detent openings 7.

In one embodiment, the threads and the spacing between the lower detents 6 and the upper detents 7 is such that a one quarter (¼) turn of the base will cause the base/reservoir unit to travel from the first to the second position. The needle 9 is disposed so that when the base/reservoir unit is in the second position, the needle pierces the septum of the reservoir 1. Thus the movement of the base/reservoir unit from the first to the second position within the cap serves to cause the needle to pierce the reservoir's septum, thus permitting the fluid in the reservoir to flow into the needle 9 and the insertion set tubing 5.

After this connection is made, the reservoir, base and cap form a unit which can be releasably secured in the housing of a medication infusion pump. (not shown) Detents 4a extend radially from the exterior of the cap and are adapted to engage into detent openings (not shown) in the pump housing. In an alternative embodiment, the cap 4 can include external threads (not shown) which are used to engage the threads of the pump housing in order to secure the reservoir/base/cap unit into the housing.

Figure 3:
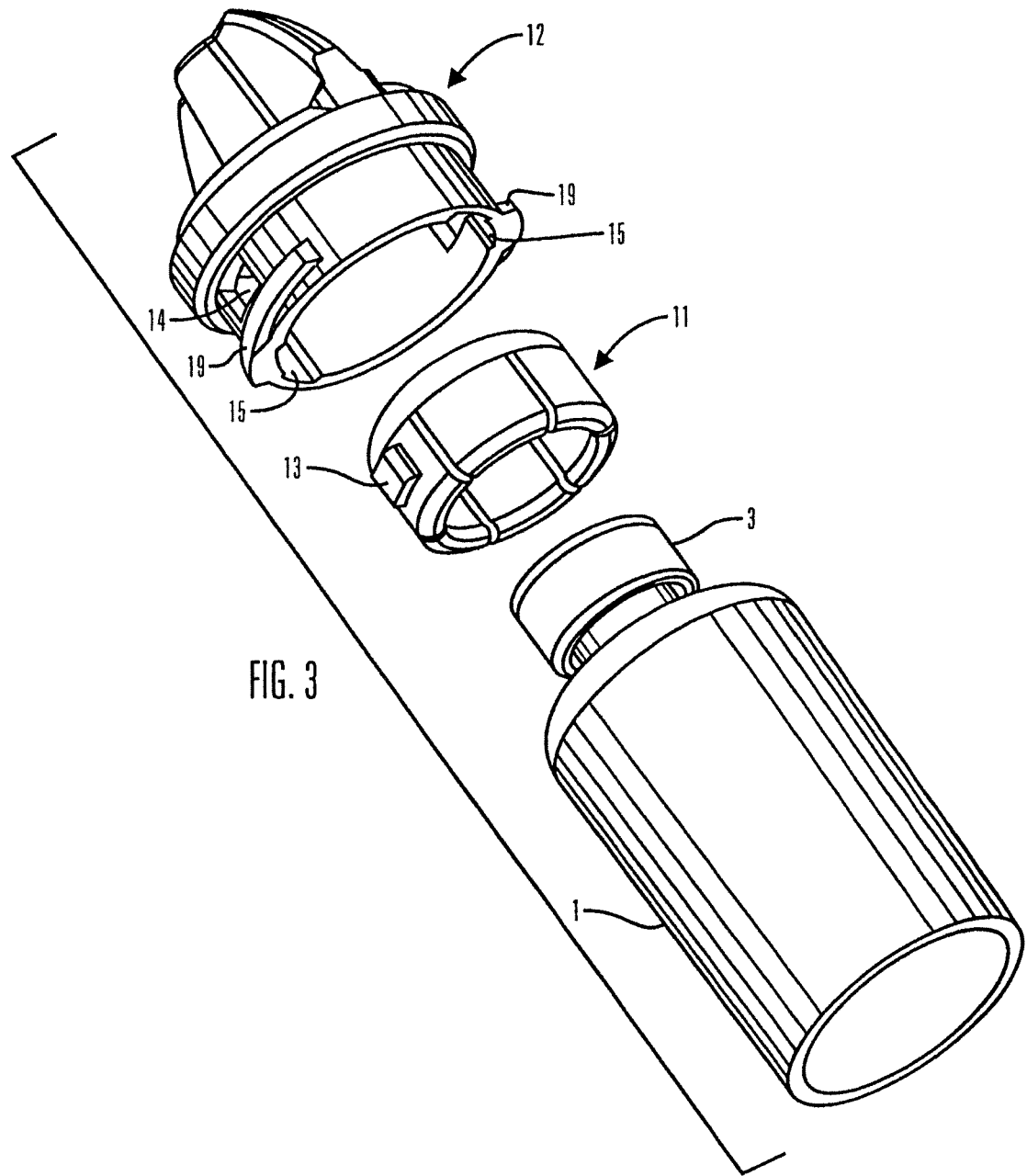
FIG. 3 is an exploded, perspective view of an alternative embodiment of a medication reservoir connection interface apparatus.
Figure 4:
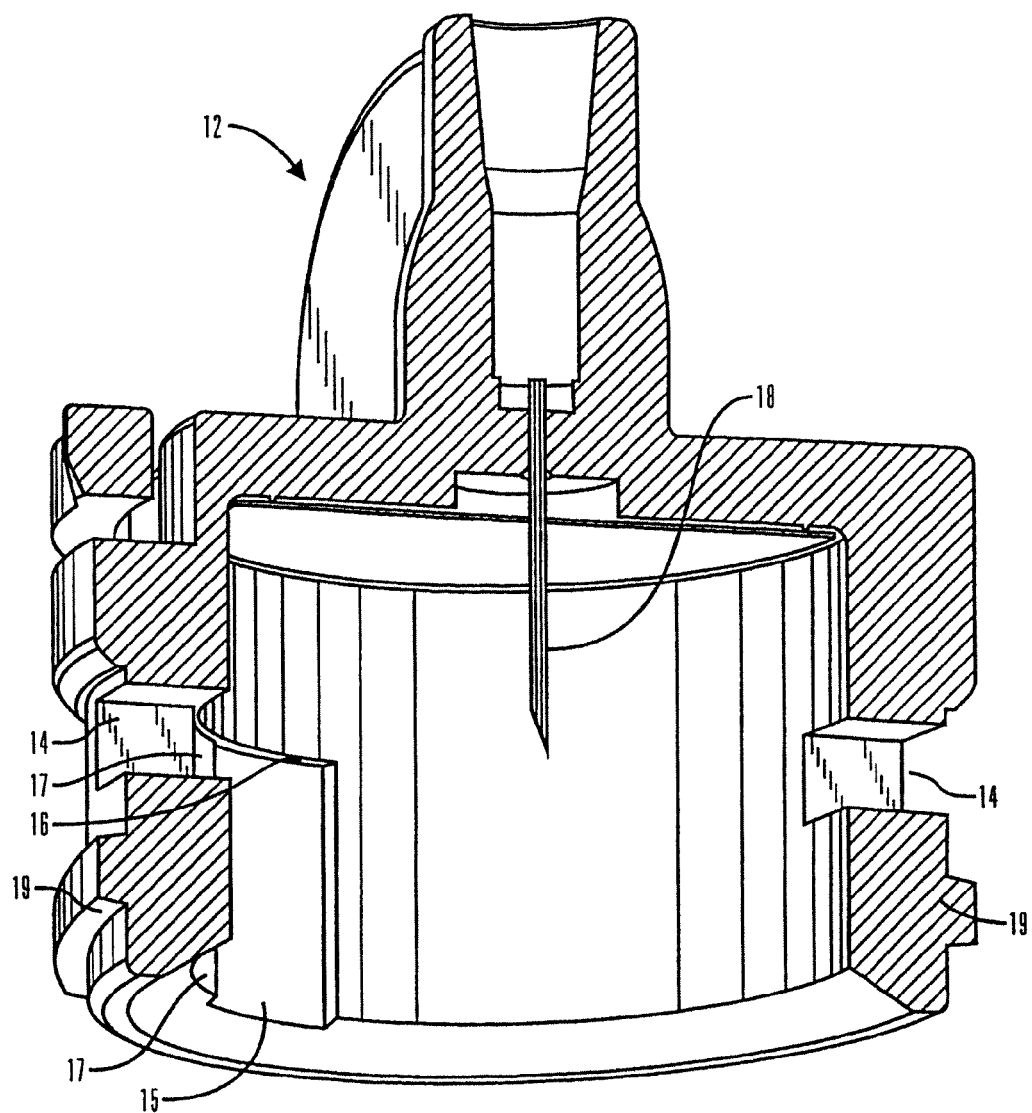
FIG. 4 is a side, cut-away view of a cap used as a medication reservoir connection interface apparatus.

FIGS. 3 and 4 show an alternative embodiment of the infusion set connector interface. The connector interface is comprised of a base 11 and a cap 12. The cap 12 includes a needle 18 located internal to the cap housing (FIG. 4). The base 11 would normally be fixedly attached to the reservoir 1 by securing it around the swage 3. However, alternative embodiments of the present invention include a removable base so that the connector interface could be used with standard reservoirs, cartridges or syringes which were not initially manufactured with the base attached.

The cap 12 portion of the connector interface is removably attached to the base 11 with a releasable coupler. In this embodiment, the releasable coupler is comprised of detents formed on the base 11 and detent openings disposed in the cap 12. Two detents 13 are disposed on the sides of the base 11 and are spaced 180° radially apart. Only one detent 13 is shown in FIG. 3. The detents 13 are sized to fit in two detent openings 14 which are formed in the cap 12. As with the pair of detents 13, each of the detent openings 14 are radially spaced apart by 180°.

In operation, the base 11 and the reservoir 1 form an integrated unit which in turn is to be connected to the cap 12. In connecting this integrated base/reservoir unit to the cap 12, the base 11 is inserted into the lower end of the cap 12. The detents 13 slide into matingly shaped and longitudinally open entry slots 15 formed within the interior walls of the cap 12.

When the base 11 is fully inserted in the cap 12, the leading edges of the detents 13 abut an annular stop shoulder 16 formed within the cap 12. After the detents 13 are in this position, the base 11 is rotated within the cap 12 toward a locked position. Referring to FIG. 4, this rotation displaces the detents 13 in a rotational direction for engagement with cam surfaces 17 formed within the cap 12. The rotational force on the detents 13 over the cam surfaces 17 provides a compression force on the detents 13. Continued rotation of the base 11 displaces the detents 13 past the cam surfaces 17 and into alignment with the detent openings 14. The detents 13 enter the detent openings 14 with a snap-action. Thus, the detents 13 are effectively locked within the detent openings 14 to prevent longitudinal separation of the base 11 from the cap 12.

In the preferred embodiment, the internal needle 18 of the cap 12 is disposed so that when the base/reservoir unit is fully inserted in the cap 12, the needle pierces the septum (not shown) of the reservoir 1. Thus the insertion force of the base/reservoir unit to the point where the detents 13 abut the annular stop shoulder 16 causes the needle 18 to pierce the septum, thus permitting the fluid in the reservoir to flow into the needle 18 and the insertion set tubing (not shown).

After this connection is made, the reservoir, base and cap form a unit which can be releasably secured in the housing of a medication infusion pump. (not shown) The cap 12 includes external threads 19 which are used to engage the threads of the pump housing in order to secure the reservoir/base/cap unit into the housing. In the preferred embodiment, the threads 19 have an eight threads per inch ("TPI"), 2 start profile. Moreover, they have a square shaped cross section which maximizes their holding strength. Other thread profiles and cross-sections may be used however.

When disconnection of the base 11 from the cap 12 is desired, the base 11 must be reverse-rotated within the cap 12, to move the detents 13 past the cam surfaces 17 into re-alignment with the entry slots 15. Such reverse-rotation of the coupler can be performed relatively easily, but essentially requires an affirmative intent by the user to disconnect the coupling. When the detents 13 are re-aligned with the entry slots 15, the cap 12 and base 11 can be separated easily with minimal longitudinal force.

Figure 5:
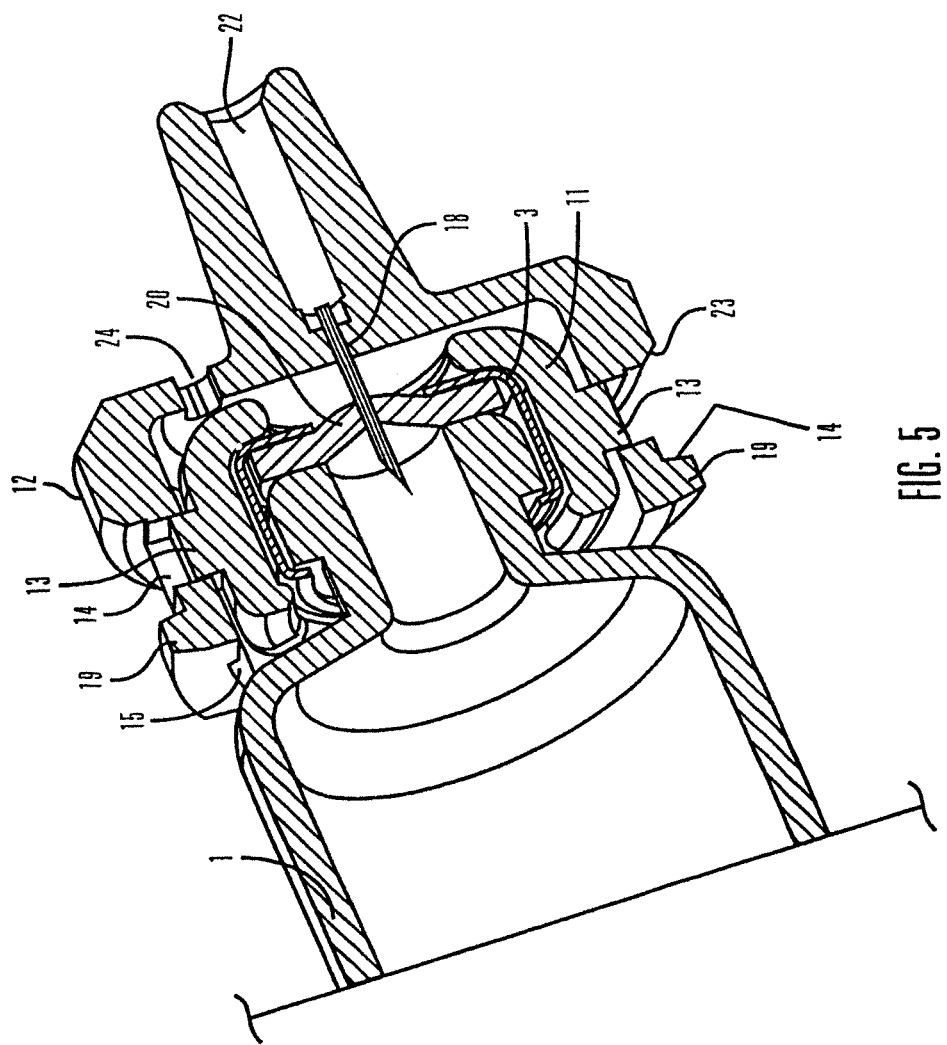
FIG. 5 is a side, plan cut-away view of a medication reservoir connection interface apparatus with a needle inserted into a reservoir.

FIG. 5 shows a cross sectional view of the reservoir/base/cap integrated unit in accordance with the embodiment of FIGS. 3 and 4. The reservoir 1 includes a crimp seal swage 3 which encloses the outer periphery of the rubber septum 20 in order to secure the septum 20 to the reservoir 1 and form a water tight seal. With the base 11 in the locked position as shown, the detents 13 of the base 11 are locked into the detent openings 14 to securely attach the base/reservoir unit into the cap 12. The needle 18 pierces the rubber septum 20, thus permitting the flow of liquid through the needle 18 and into the infusion set tubing cavity 22. Infusion set tubing (not shown) is secured into the cavity 22 to allow the liquid to continue its flow to the user.

In the preferred embodiment, the conduit from the cap 12 is infusion set tubing. However in an alternative embodiment, the conduit comprises a second needle (not shown). This is secured into the cavity 22 with the point of the second needle extending outward. With this arrangement, the connector serves as an apparatus for permitting the refilling of the reservoir 1. The second, external needle would pierce the septum of a supply vial of fluid. The fluid could then be drawn into the cap in a reverse flow and into the reservoir 1 via the internal needle 18.

In the embodiment shown in FIG. 5, infusion set tubing is secured to the cavity 22 to allow liquid to flow to the user. The cavity 22 is disposed in the raised portion of the cap 12. In an alternative embodiment, however, the raised portion of the cap 12 can be in the shape of a standard luer fitting 47 shown in FIG. 13.

Referring to FIG. 5, in one embodiment the base 11 is formed around and fixedly attached to the crimp seal swage 3 portion of the reservoir 1. In an alternative embodiment, however, the base 11 is not fixedly attached to the reservoir. Rather, the base 11 is a separate unit which is adapted to be releasably secured to the reservoir via a friction fit. This arrangement permits the connector apparatus to be used with standard reservoirs.

Still referring to FIG. 5, the cap 12 includes threads 19 for securing the assembly into the pump housing (not shown). A shoulder 23 is formed as part of the cap 12 and is adapted to seat against the pump housing to form a water tight seal. This prevents any water which is exterior to the housing from entering, thus permitting the user to engage in water sports.

The construction of these pumps to be water resistant can give rise to operational problems. As the user engages in activities which expose the pump to varying atmospheric pressures, such as for example, swimming or traveling in an air plane, differential pressures can arise between the interior of the air tight/water-resistant housing and the atmosphere. Should the pressure in the housing exceed external atmospheric pressure, the resulting forces could cause the reservoir piston to be driven inward thus delivering unwanted medication. Alternatively, should the pressure in the housing be less than the external pressure, the resulting forces could cause the infusion pump motor to work harder to advance the reservoir piston.

To address this problem, a preferred embodiment of the invention includes a vent which permits water resistant housing construction. The cap 12 includes a plurality of vent ports 24, only one of which is shown in FIG. 5. The vent ports 24 permit equalization of pump housing pressure to atmospheric pressure. Hydrophobic material (not shown) covers the interior openings of the vent ports 24. Hydrophobic material permits air to pass through the material while preventing water or other liquids from doing so, thus permitting water resistant venting. The preferred embodiment uses a hydrophobic material such as Gore-Tex®, PTFE, HDPE, or UHMW polymers from sources such as W.I. Gore & Associates, Flagstaff, Ariz., Porex Technologies, Fairburn, Ga., DeWAL Industries, Saunderstown, R.I., or Pall Specialty Materials, Port Washington, N.Y.

These materials are available in sheet form or molded (press and sintered) in a geometry of choice. Referring to FIGS. 14a-14c, preferred methods to attach this material to the cap 12 include molding the hydrophobic material into a sphere 50 (FIG. 14a) or a cylinder 51 (FIG. 14b) and pressing it into a cavity in the pre-molded plastic housing. Alternatively, a label 52 (FIG. 14c) of this material could be made with either a transfer adhesive or heat bond material 53 so that the label could be applied over the vent port 24. Alternatively, the label could be sonically welded to the housing. In either method, air will be able to pass freely, but water will not.

In an alternative embodiment which is not shown, the venting is accomplished through a vent port located in the pump housing. This is described in greater detail in copending application Ser. No. 09/429,352 filed concurrently herewith, which application is incorporated by reference in its entirety. Alternatively, vent ports can be placed both in the cap 12 as well as the pump housing.

An advantage of placing the vent port and hydrophobic material in the cap 12, as opposed to in the pump housing only, is that the infusion set and its related connectors are disposable and are replaced frequently with each new reservoir or vial of medication. Thus, new hydrophobic material is frequently placed into service. This provides enhanced ventilation as compared with the placement of hydrophobic material in only the pump housing. Material in this location will not be replaced as often and thus is subject to dirt or oil build up which will retard ventilation.

As an alternative to the use of hydrophobic material, water can be prevented from flowing through the vent port by other apparatuses, such as the use of relief valves.

Figure 6:
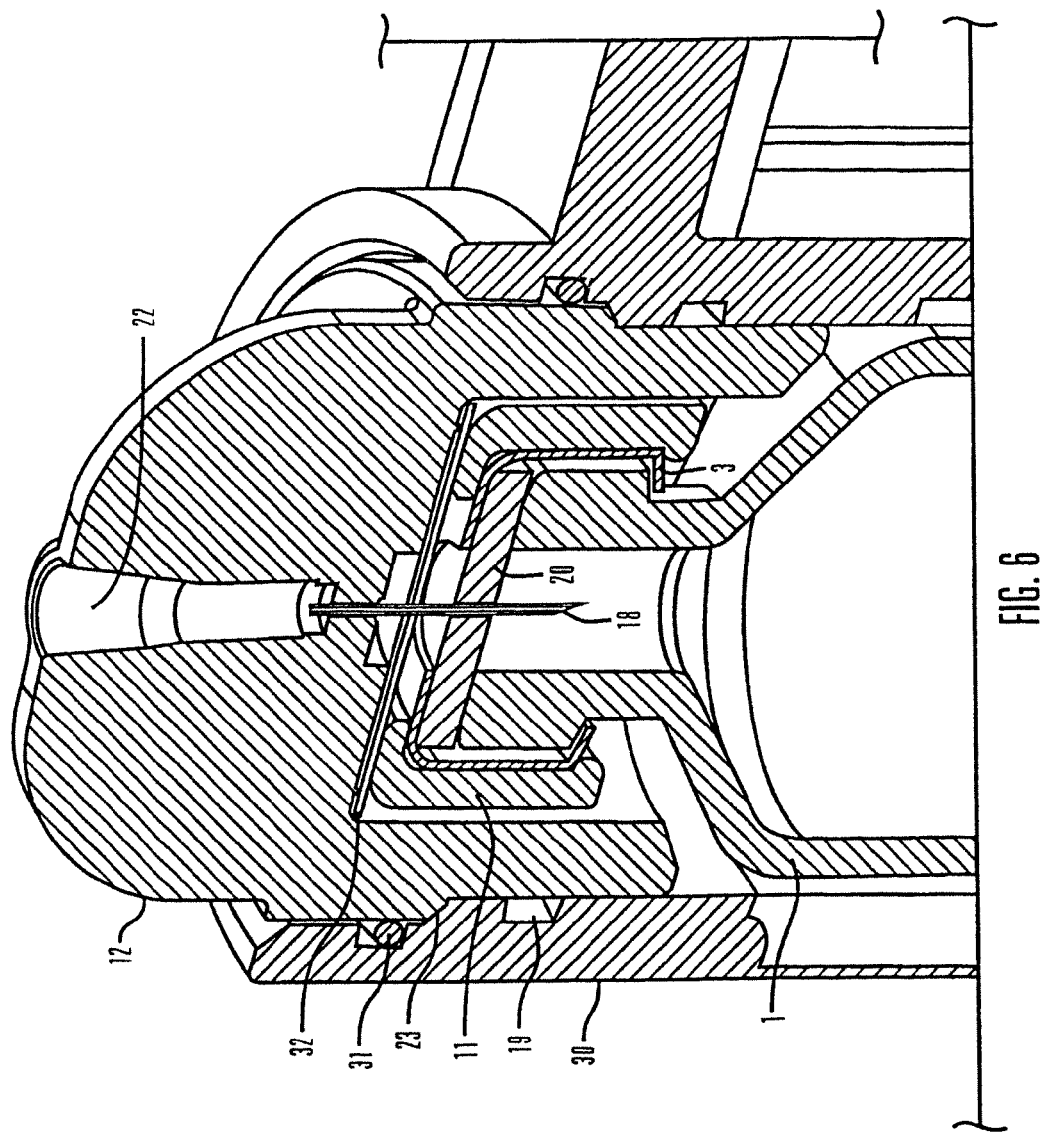
FIG. 6 is a side, plan cut-away view of a medication reservoir connection interface apparatus which is inserted into a pump housing.

FIG. 6 shows a cross-sectional view of the reservoir/base/cap unit in accordance with the embodiment of FIGS. 3 and 4 which is secured into a pump housing 30. The threads 19 of the cap 12 engage the pump housing threads. Rather that the use of threads, an alternative embodiment (not shown) of the cap 12 could include detents extending radially from the exterior of the cap 12 which are adapted to engage detent openings in the pump housing.

The shoulder 23 portion of the cap 12 seats against the pump housing 30 to permit water tight construction. Further aiding in the water tight construction is an O-ring seal 31 which is disposed in the pump housing 30 and located just above the shoulder 23. In the preferred embodiment, the vent material 32 is comprised of hydrophobic material and is sonic welded to the upper interior surface of the cap 12. Alternatively, the vent material 32 could be attached to the cap 12 with an adhesive. The vent ports are not shown in FIG. 6.

Although the foregoing description of the venting was in connection with the embodiment of FIGS. 3-6, this feature is also applicable to the embodiment of FIGS. 1-2.

Figure 7:
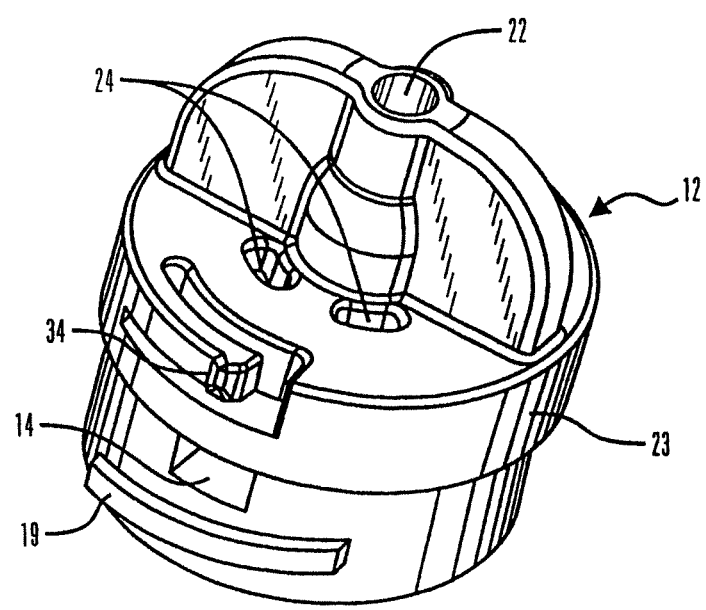
FIG. 7 is a perspective view of an alternative embodiment of a medication reservoir connection interface apparatus.
Figure 8:
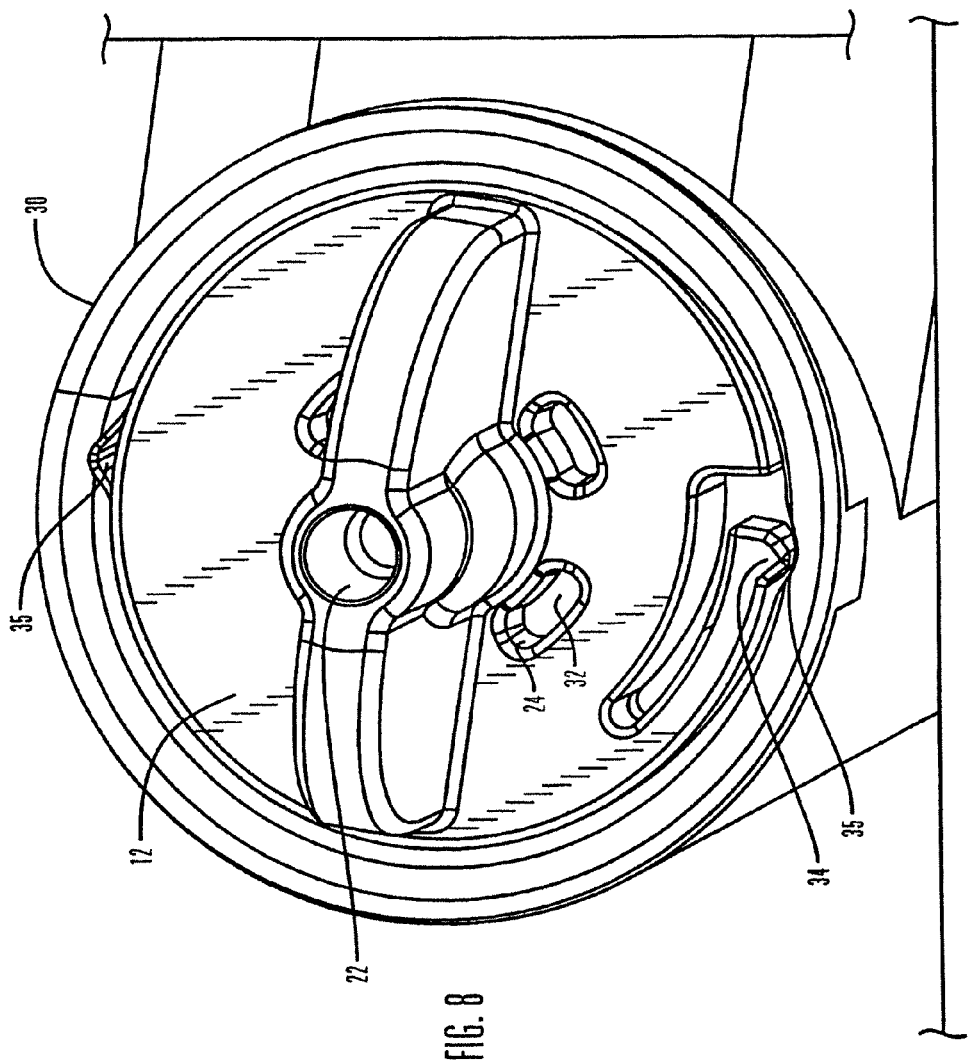
FIG. 8 is a perspective top view of an alternative embodiment of a medication reservoir connection interface apparatus which is secured into a pump housing.

FIGS. 7 and 8 show an alternative embodiment of the cap 12. Referring to FIG. 7, a cap engagement member consists of a detent arm 34 which is formed in the upper portion of the cap 12. The purpose of the detent arm 34 is to securely engage the cap 12 into the pump housing. FIG. 8 shows a top view of the cap 12 positioned in the pump housing 30. The pump housing 30 has two case lock recesses 35 disposed in the circular rim of the housing. The detent arm 34 snaps into either of the case lock recesses 35. This engagement results in a "click" when the cap 12 is appropriately seated, thus providing both tactile and audible feedback to the user that the cap is securely engaged in the pump housing. Moreover, the detent arm 34 aligning with the recess 35 also serves as a visual indicator that the cap 12 is appropriately seated.

Figure 9:
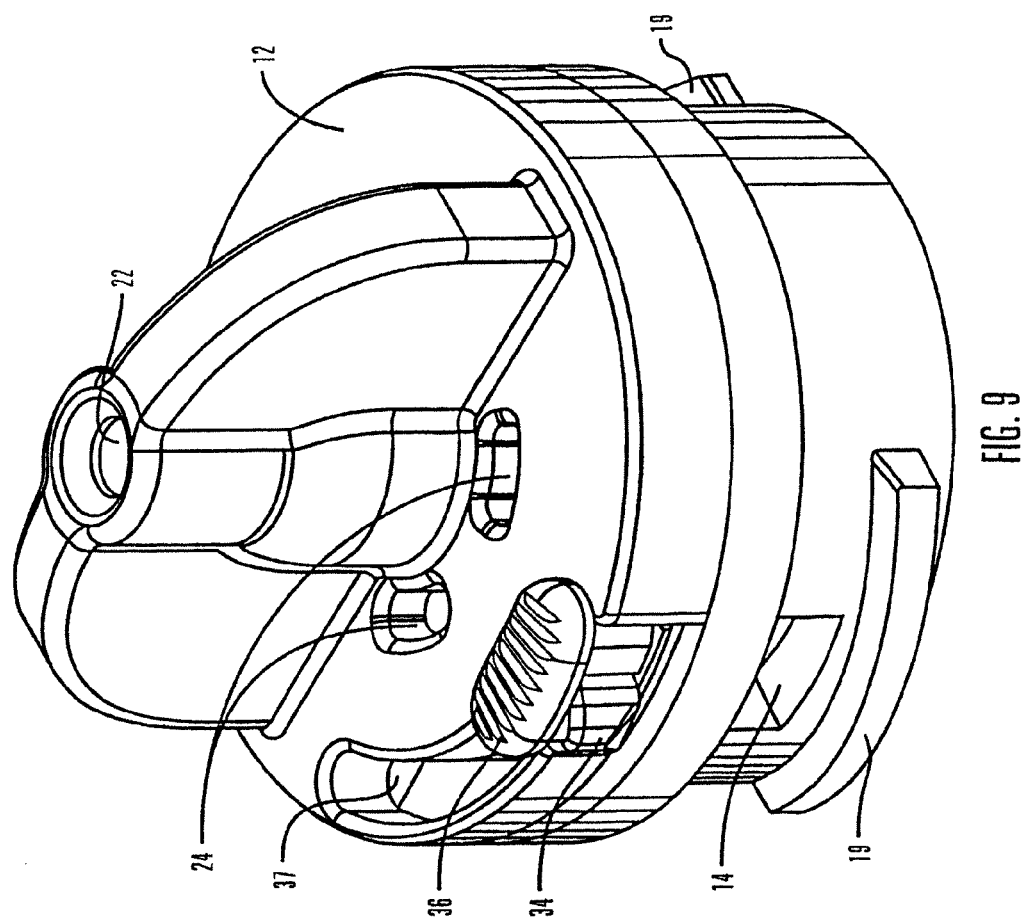
FIG. 9 is a perspective view of an alternative embodiment of a medication reservoir connection interface apparatus.

FIG. 9 shows an alternative embodiment of the cap 12 which contains a child safety feature. The cap 12 includes a locking member which consists of a safety tab 36 disposed in a groove 37. The safety tab 36 is sized such that it is able to slide along the length of the groove 37. When the safety tab 36 is in the position shown in FIG. 9, the detent arm 34 is unable to retract from its engaged position. Thus when the cap 12 is seated into the pump housing 30 (not shown) and the detent arm is seated into the case lock recess 35 (not shown), the safety tab 36 will prevent the detent arm 34 from disengaging from the case lock recess 35 thus more securely locking the cap 12 in the pump housing.

Thus for example, a parent could slide the safety tab 36 from the unlocked location in the groove 37 to the locked location shown in FIG. 9 so that it would be more difficult for a young child or infant to inadvertently remove the cap/base/reservoir unit from the pump housing. On the other hand, when the safety tab 36 is moved to the opposite end of the groove 37, the detent arm 34 is able to retract thus permitting removal of the cap 12 from the pump housing.

Although the foregoing description of the cap engagement member and child safety tab was in connection with the embodiment of FIGS. 3-9, this feature is also applicable to the embodiment of FIGS. 1-2.

Figure 10:
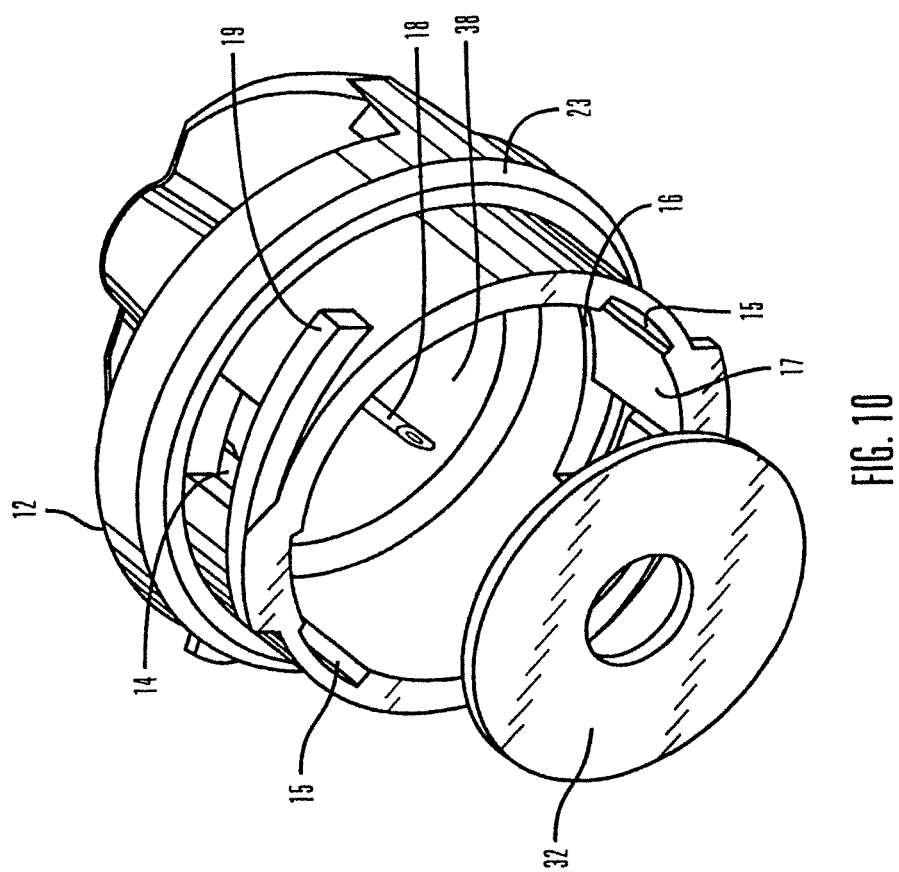
FIG. 10 is an exploded, perspective view of a cap used as a medication reservoir connection interface apparatus.

FIG. 10 shows an exploded view of the cap 12 and the vent material 32. In the preferred embodiment, the vent material is made of hydrophobic material and is formed in a circular shape with a circular hole in the center. The vent material 32 is attached to the upper interior surface 38 of the cap 12 via sonic welding or an adhesive. When it is so attached, the needle 18 protrudes through the center hole of the vent material 32 but the interior openings of the vent ports 24 (not shown) are covered.

Figure 11:
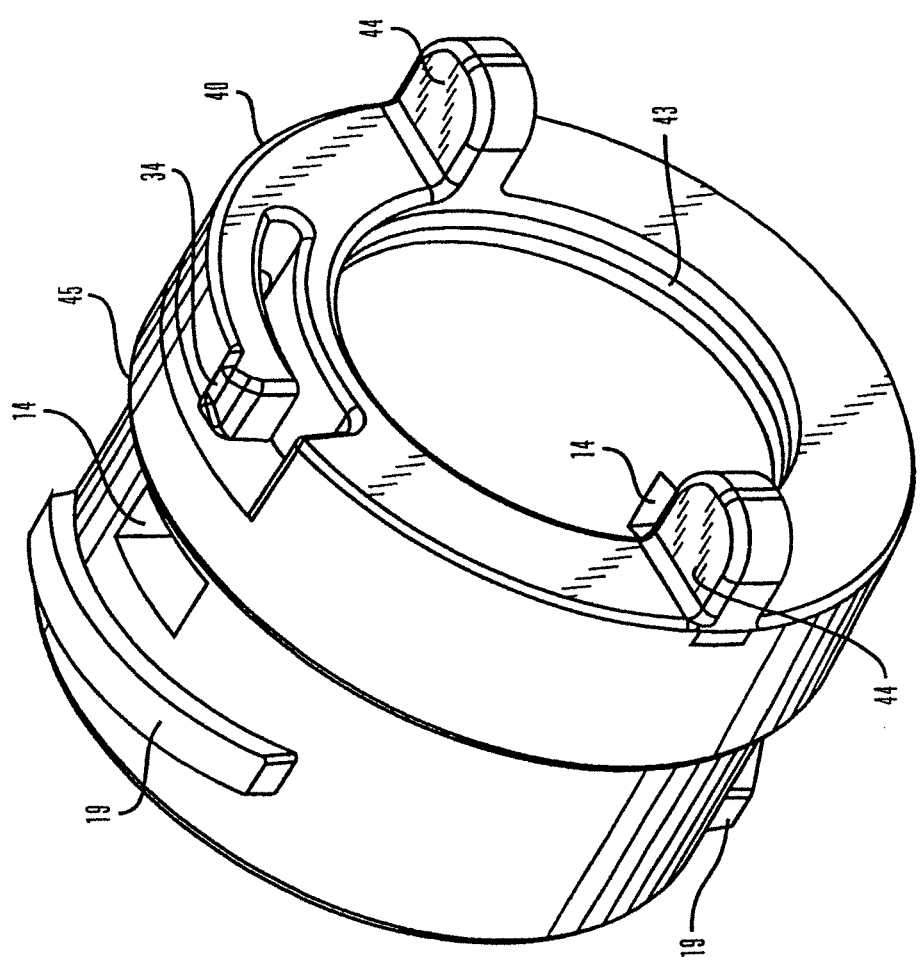
FIG. 11 is a perspective view of a medication reservoir connection interface adapter.
Figure 12:
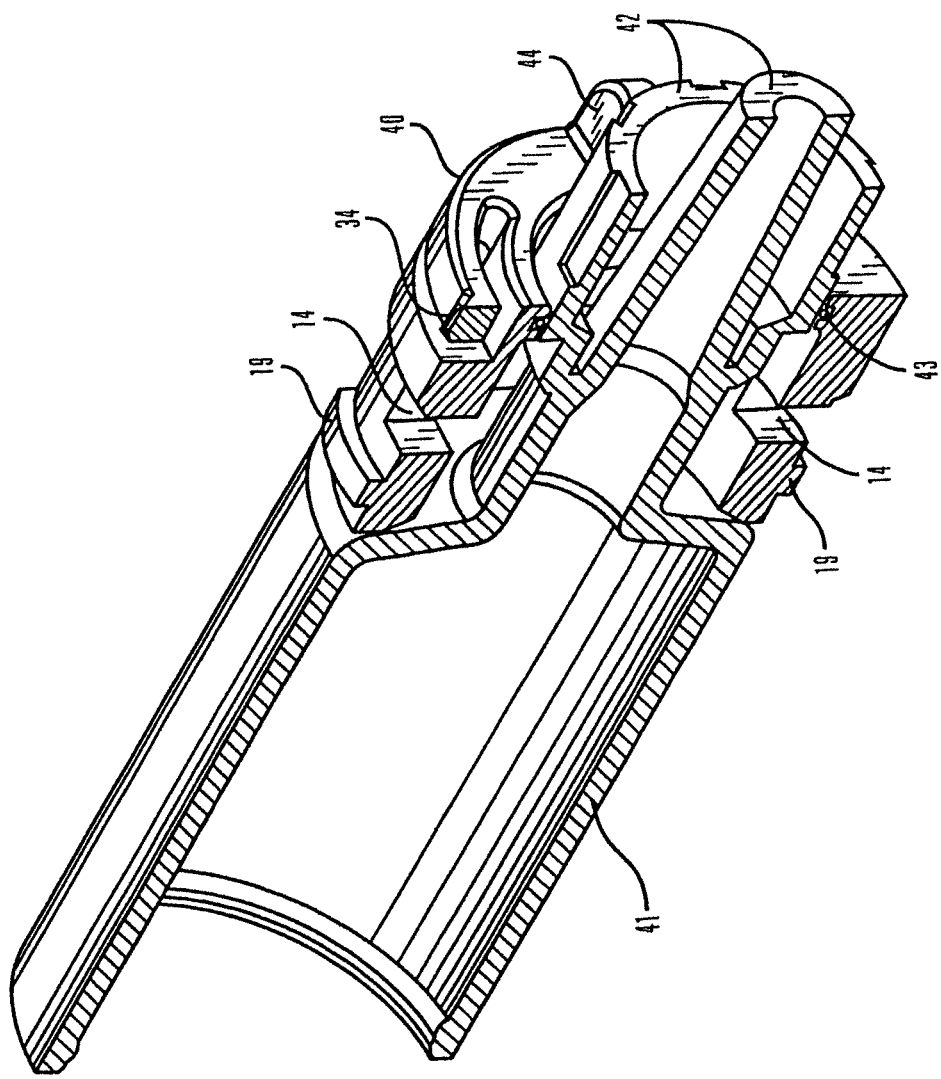
FIG. 12 is a cross-sectional view of a medication reservoir connection interface adapter.

FIGS. 11 and 12 show an embodiment of the present invention where an adapter is provided to allow a standard style syringe 41 with an integrated luer fitting 42 to be mounted and sealed in the pump housing. The syringe 41 is inserted through the center of the adapter 40 and held into place by a friction fit. The O-ring seal 43 in the adapter 40 seats against the syringe wall in order to prevent water and dirt from entering the pump housing.

A shoulder 45 is formed as part of the adapter 40 and is adapted to seat against the interior of the pump housing to form a water tight seal. Two tabs 44 are formed on the top surface of the adapter 40 and provide a surface for the user to grip the adapter 40 and twist it so that the adapter threads 19 engage the threads (not shown) of the pump housing. A detent arm 34 is formed in the upper portion of the adapter 40. Its purpose is to securely lock the adapter 40 into the pump housing (not shown) in the same manner as is shown in FIG. 8. Although not shown in FIGS. 11 and 12, the adapter 40 can further contain vent ports covered with hydrophobic material or a relief valve in order to permit water resistant venting of the pump housing in the same manner as previously described with other embodiments.

FIG. 13 shows another embodiment of the present invention where an interface is provided to connect a reservoir to a conduit, such as tubing, via a standard luer fitting connection. This allows a luer style disposable infusion set to connect to the pump housing (not shown). A cap 46 is formed with a luer fitting 47 portion as an integral part thereof. Except for the shape of the luer fitting 47 portion, the cap 46 has all of the other features of the cap 12 shown in FIG. 5. Thus referring to FIG. 13, the cap 46 is comprised of, among other things, threads 19, detent openings 14, a shoulder 23, vent ports 24, a detent arm 34, and a needle (not shown) disposed in the interior of the cap 46.

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims rather than the foregoing description, and all changes which come within the meaning and range of equivalency of the claims are therefore intended to be embraced therein.

What is claimed is:

1. A method of connecting a cylindrical fluid medication reservoir to a medication pump housing and infusion set tubing, the method comprising releasably coupling the cylindrical fluid medication reservoir to the medication pump housing a system comprising:

a housing engagement interface having a substantially cylindrical shape and comprising a detent arm, wherein the housing engagement interface is adapted to secure a cylindrical fluid medication reservoir within the medication pump housing, infusion tubing adapted to connect with the housing engagement interface;

a medication pump housing adapted to receive the cylindrical fluid medication reservoir, wherein:

the medication pump housing comprises a circular rim having a lock recess disposed in the rim; and the cylindrical fluid medication reservoir is connected to the medication pump housing by rotating the housing engagement member within the medication pump housing so that the detent arm snaps into the case lock recess.

2. The method of claim 1, wherein the detent arm is disposed on the housing engagement interface so that the detent arm snaps into the case lock recess and provides tactile or audible indication to a user that the housing engagement interface is operatively seated in the medication pump housing.

3. The method of claim 1, wherein the detent arm is disposed on the housing engagement interface so that aligning the detent arm with the case lock recess provides a visual indication that the housing engagement interface is operatively seated in the medication pump housing.

4. The method of claim 1, wherein the infusion tubing is connected with the housing engagement interface prior to connecting the housing engagement interface to the medication pump housing.

5. The method of claim 1, wherein the circular rim of the medication pump housing comprises two case lock recesses disposed in a 180° orientation.

6. The method of claim 1, wherein the medication pump housing comprises a housing thread member disposed in the housing an adapted to engage an interface thread member disposed on the housing engagement interface.

7. The method of claim 1, wherein the housing engagement interface comprises a first tab and a second tab disposed at the first end of the housing engagement interface so as to provide a first and a second surface for a user to grip and twist the housing engagement interface in order to engage the housing engagement member with the medication pump housing.

8. The method of claim 1, wherein the housing engagement interface comprises a vent that permits the passage of air and inhibits the passage of fluids.

9. The method of claim 1, wherein the housing engagement interface comprises a safety tab disposed on the interface so that when the interface is seated into the medication pump housing, the safety tab prevents the detent arm from disengaging from the case lock recess.

10. The method of claim 1, wherein the housing engagement interface comprises:

a housing engagement member comprising the detent or a thread projecting outward from a cylindrical external surface of the housing engagement interface and adapted to engage an engagement member disposed in a housing recess within the infusion device, wherein the housing engagement interface connects with the fluid medication reservoir and both the housing engagement interface and the fluid medication reservoir at least partially fit inside the housing recess of the infusion device and are insertable and removable from the housing recess within the infusion device upon rotation of the housing engagement interface;

a conduit cavity adapted to secure the infusion tubing to the housing engagement interface; and a vent that permits the passage of air and simultaneously inhibits the passage of fluids so as to permit fluid resistant venting of air through the vent and equalization of pressure inside the medication pump to atmospheric pressure outside the medication pump.

11. A method of connecting a cylindrical insulin reservoir to an insulin pump housing and infusion set tubing so as to deliver insulin to a patient, the method comprising:

(a) coupling the cylindrical insulin reservoir to the insulin pump housing a system comprising:

a housing engagement interface having a substantially cylindrical shape and comprising a detent arm, wherein the housing engagement interface is adapted to secure a cylindrical insulin reservoir within the insulin pump housing, infusion tubing adapted to connect with the housing engagement interface;

a insulin pump housing adapted to receive the cylindrical insulin reservoir, wherein:

the insulin pump housing comprises a circular rim having a lock recess disposed in the rim; and the cylindrical insulin reservoir is connected to the insulin pump housing by rotating the housing engagement member within the insulin pump housing so that the detent arm snaps into the case lock recess; and (b) actuating the insulin pump so that insulin is delivered to the patient.

12. The method of claim 11, wherein the infusion set tubing is coupled to a needle or a catheter.

13. The method of claim 1, wherein a needle is disposed within the cylindrical insulin reservoir when the infusion set tubing is connected with the housing engagement interface and the housing engagement interface is coupled and operatively engaged with the cylindrical insulin reservoir.

14. The method of claim 13, wherein the needle is disposed in an axis around which the housing engagement interface rotates to releasably secure the housing engagement interface within the insulin pump housing.

15. The method of claim 11, wherein the housing engagement interface comprises a first tab so as to provide a first surface for a user to grip and twist the interface to engage the interface with the insulin pump upon rotation of the interface, wherein the first tab projects outward from the interface such that the first surface of the first tab is disposed in an orientation perpendicular to a plane defined by the circumference of the interface.

16. The method of claim 11, wherein the infusion tubing is connected with the housing engagement interface following connecting the housing engagement interface to the medication pump housing.

17. The method of claim 11, wherein the circular rim of the insulin pump housing comprises two case lock recesses disposed in a 180° orientation.

18. The method of claim 11, wherein the insulin pump housing comprises a housing thread member disposed in the housing an adapted to engage an interface thread member disposed on the housing engagement interface.

19. The method of claim 11, wherein the housing engagement interface comprises a vent that permits the passage of air and inhibits the passage of fluids.

20. The method of claim 19, wherein the vent comprises a hydrophobic material.

* * * * *